United States Patent [19]

Hayes

[11] Patent Number: 4,885,811
[45] Date of Patent: Dec. 12, 1989

[54] PROTECTING BODIES DURING TRANSIT

[76] Inventor: Michael L. Hayes, 4722 Donegal, Corpus Christi, Tex. 78411

[21] Appl. No.: 197,439

[22] Filed: May 23, 1988

Related U.S. Application Data

[63] Continuation-in-part of Ser. No. 910,682, Sep. 23, 1986, abandoned.

[51] Int. Cl.⁴ .............................................. A61G 1/00
[52] U.S. Cl. .......................................... 5/82 R; 5/431; 5/450; 128/89 R; 128/870
[58] Field of Search ......... 5/82 R, 449, 450, 453–455, 5/431, 446, 447; 128/87 R, 88, 89 R, 134, 402, DIG. 20, 846, 870; 206/522, 524.8, 584

[56] References Cited

U.S. PATENT DOCUMENTS

| | | | |
|---|---|---|---|
| 3,315,621 | 4/1962 | Creelman | 128/134 |
| 3,515,267 | 6/1970 | Rocca et al. | 206/584 |
| 3,667,593 | 6/1973 | Pendleton | 206/584 |
| 3,745,998 | 6/1973 | Rose | 128/89 R |
| 3,762,404 | 10/1973 | Sakita | 128/89 R X |
| 3,901,225 | 8/1975 | Sconce | 128/402 X |
| 4,182,320 | 1/1980 | Sweeney | 128/89 R |
| 4,301,791 | 11/1981 | Franco, III | 5/82 R X |
| 4,583,253 | 4/1986 | Hall | 5/424 X |
| 4,624,248 | 11/1986 | Poole et al. | 128/89 R |

Primary Examiner—Michael F. Trettel
Attorney, Agent, or Firm—G. Turner Moller

[57] ABSTRACT

A restraint comprises a multiplicity of flexible bubbles which are encased in an air-tight envelope of film material. The bubbles are soft, having a Shore A Durometer rating of 10 or less. When air inside the envelope is withdrawn, the restraint molds to the shape of the animate or inanimate object which it surrounds. The restraint becomes surprising rigid but remains soft and pliable. Another embodiment of the invention is particularly designed as an infant carrier.

15 Claims, 8 Drawing Sheets

Figure 18

PROTECTING BODIES DURING TRANSIT

This application is a continuation-in-part of application Ser. No. 06/910,682, filed Sept. 23, 1986 now abandoned.

This invention relates to a technique for protecting a body, animate or inanimate, during transit.

The problem is to provide a soft cushioned environment or enclosure for objects or people which vary in size and shape. Broadly, the approach is to provide a carrier or mat which can be shaped at the point of use to conform, more or less, to the object or person being handled. More specifically, the invention uses flexible bubbles encased in an impermeable film material which allows the device to mold to the shape of the object it encloses affording a protective cushion as air is evacuated from the device. Because the bubbles are themselves soft, the device remains soft even when the air is evacuated from the envelope containing the bubbles.

When manufactured in vacuum mat application, this invention protects animate and inanimate objects which need special care in transfer and handling. The device may be disposable or reuseable.

When manufactured as an infant restraint with the addition of a built in backboard, and used with either a basic closure or a harness, the device of this invention becomes a protective environment for premature infants, neonates and other types of patients. As such, this invention has application as a transport restraint and as a medical restraint for invasive and noninvasive procedures. The transparent material allows the constant visual monitoring of skin color of the limbs and the open center allows access to the trunk, head, neck and groin of the patient for emergency medical procedures. Other advantages of this invention include a thermal insulating quality, due to the cellular inner construction of the device, which helps maintain body temperature. As a patient handling device, it reduces the amount of direct handling required in caring for the patient, thereby reducing exposure of the patient to hospital acquired infections and reducing other patient complications resulting from handling stress. In addition, the same properties which provide thermal insulation also provide sound deadening properties which reduces patient stress from noise exposure. The built in backboard of the infant restraint makes anti-shock positioning possible, i.e. the patient's feet can be placed above the heart and head.

Optional pockets on the center bladder in the upper right and left side may contain a continuous loop recording of the mother's body sounds and voice to soothe an infant. Another pocket may contain a dosimeter for X-rays as the transparent properties of the device allows X-rays and other similar tests of the infant while in the restraint system.

With some minor adaptation, the device of this invention can be used to transport and restrain infant airplane passengers It is an object of this invention to provide an improved technique for handling and/or transporting animate and inanimate objects.

A more specific object of this invention is to provide a body cushioning device comprising a multiplicity of soft gas filled bubbles enclosed in an impermeable evacuable membrane. Other objects and advantages of this invention will become more fully apparent as this description continues, reference being made to the accompanying drawings and appended claims.

Referring to FIGS. 1-4, a plain vacuum mat 1 comprises a top sheet 2 of flexible gas impermeable transparent material, a multiplicity of flexible transparent fluid filled cells or bubbles 3 and a bottom sheet of similar flexible transparent material containing a stoma 5 where a piece of flexible surgical tubing 5a is inserted. The sheets are joined into an envelope in an airtight manner so that a vacuum is created when the air is removed therefrom.

Figure 1:
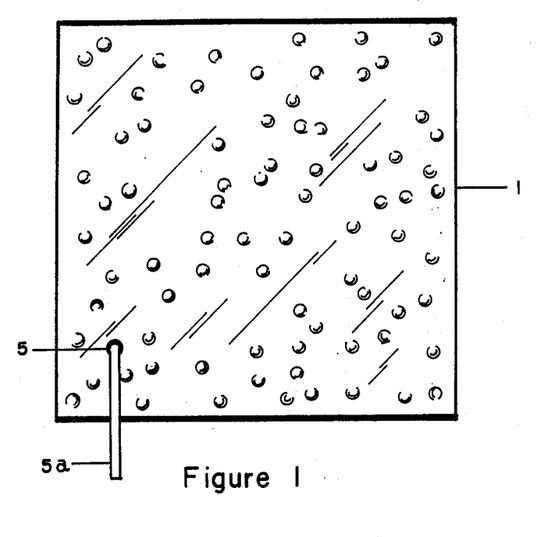
FIG. 1 is a top view of a plain vacuum mat.
Figure 2:
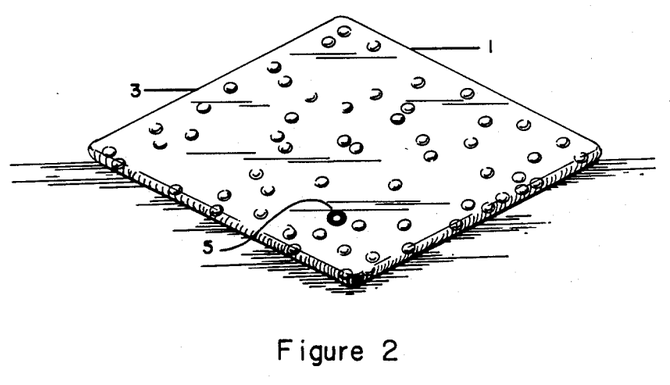
FIG. 2 is a perspective view of the plain mat of FIG. 1.

The mat 1, for some applications, will be constructed as a single sealed envelope as illustrated in FIGS. 1 and 2. In other applications, the envelope is divided into sections as more fully disclosed hereinafter. The mat 1 may be of any suitable size although its width and length are substantially greater than its thickness. Although the mat 1 is illustrated to be square or rectangular, its shape may vary substantially to include other polygonal shapes, circles and the like.

Figure 3:
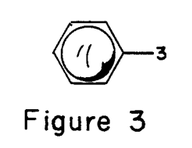
FIG. 3 is a top view of an individual flexible bubble.
Figure 4:
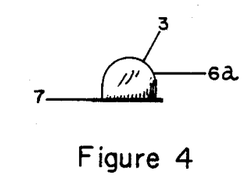
FIG. 4 is a side view of the flexible bubble of FIG. 3.

In FIGS. 3 and 4, the cells or bubbles 3 are more full shown. The bubbles 3 are independently movable and are resilient and transparent for purposes more fully apparent hereinafter. The bubbles 3 may be of any suitable type and conveniently comprise a dome or spherical shaped top 6a and a planar base 7. The top 6a and base 7 are made of an impermeable polymeric film such as polyvinyl chloride, polyethylene, polypropylene and the like. The bubbles 3 may be made in any suitable manner, such as by the same process used to manufacture conventional sheet packing material having similar bubbles incorporated therein, such as is available from Sealed Air Corporation of Arlington, Tex. In a prototype of this invention, the bubbles 3 were obtained by cutting them out of the conventional sheet packing material provided by Sealed Air Corporation.

The envelope of the mat 1 is not completely filled with the cells or bubbles 3 because, if it were, the mat 1 could not be folded or wrapped around a body to be protected. Instead, the volume of the mat 1 is substantially greater than the volume of the cells 3. Typically, the mat 1 is filled within a range of 50-80% with the cells 3.

The mat 1 may be of any suitable size, i.e. length and width, to accommodate the article to be protected. The thickness of the mat 1 is substantially less than the length or width and typically is on the order of less than 1/10th the length or width. From another viewpoint, the mat 1 is typically no more than 1-5 times thicker than the cells 3, depending on the size thereof. Typically, as the cells 3 become smaller, the thickness is a larger multiple. The cells 3 are of any suitable size and preferably are larger than $\frac{1}{4}''$ across and preferably are in the range of $\frac{1}{2}''$-$1\frac{1}{2}''$ across. From a practical standpoint, the cells are typically air filled although other suitable gases or gas-liquid mixtures are eminently suitable. When using the device of this invention as an infant carrier, it is often desirable to provide some of the cells 3 with heat generating or heat absorbing materials which may be activated by manual pressure through the envelope.

Another important characteristic of the cells or bubbles 3 is that they are soft. In contrast to this invention, evacuable splints are known which, when evacuated, become hard and rigid as is necessary in a splint. The reason this type splint becomes hard and rigid is that the articles inside the evacuable membrane are hard, or relatively hard when compared with the gas filled bubbles 3. A series of Shore A Durometer tests were run on a plurality of bubbles 3 typical of this invention and on styrofoam packing materials, which are manufactured to be about as soft a foam material as is available, as shown in Table I:

TABLE I

| Air filled Bubbles | Styrofoam Packing Elements |
| --- | --- |
| 5 | 15 |
| 6 | 18 |
| 5 | 20 |
| 5 | 16 |
| 6 | 18 |
| Average 5.4 | Average 17.4 |

There was a large variation in the readings of the styrofoam packing elements for two reasons: (1) several different types of elements were tested, some of which were sections of a sphere and some of which were more "peanut" shaped; and (2) some of the packing elements were clearly softer in one direction than in another.

On the other hand, there was little variation in the readings of the air filled bubbles because they were selected from a single sheet of packing material. It would not be surprising for bubbles from a different manufacturer to be different, but within a small range. In any event, it is apparent that the gas filled bubbles 3 of this invention are measurably softer than even the softest foam elements that could be found. Thus, the device of this invention is considerably softer and more resilient when evacuated than an evacuable splint, which is by necessity hard and rigid when in use. Although the softness of the air filled bubbles may vary somewhat, for the resultant device to be soft and resilient, the bubbles 3 have to measure less than about 10 on the Shore A Durometer. In another way of defining the bubbles 3, they contain substantially no solids.

To use the mat 1, it is wrapped about an article to be protected and the air inside the envelope is withdrawn, either by pumping air out through the tubing 5a or sucking it out. The tube 5a is then sealed, either with a conventional removable closure (not shown) or by thermally closing the end of the tubing 5a. The air withdrawn from the envelope causes the sheets to collapse onto the cells 3 to provide a surprisingly sturdy enclosure about the article to be protected.

Figure 5:
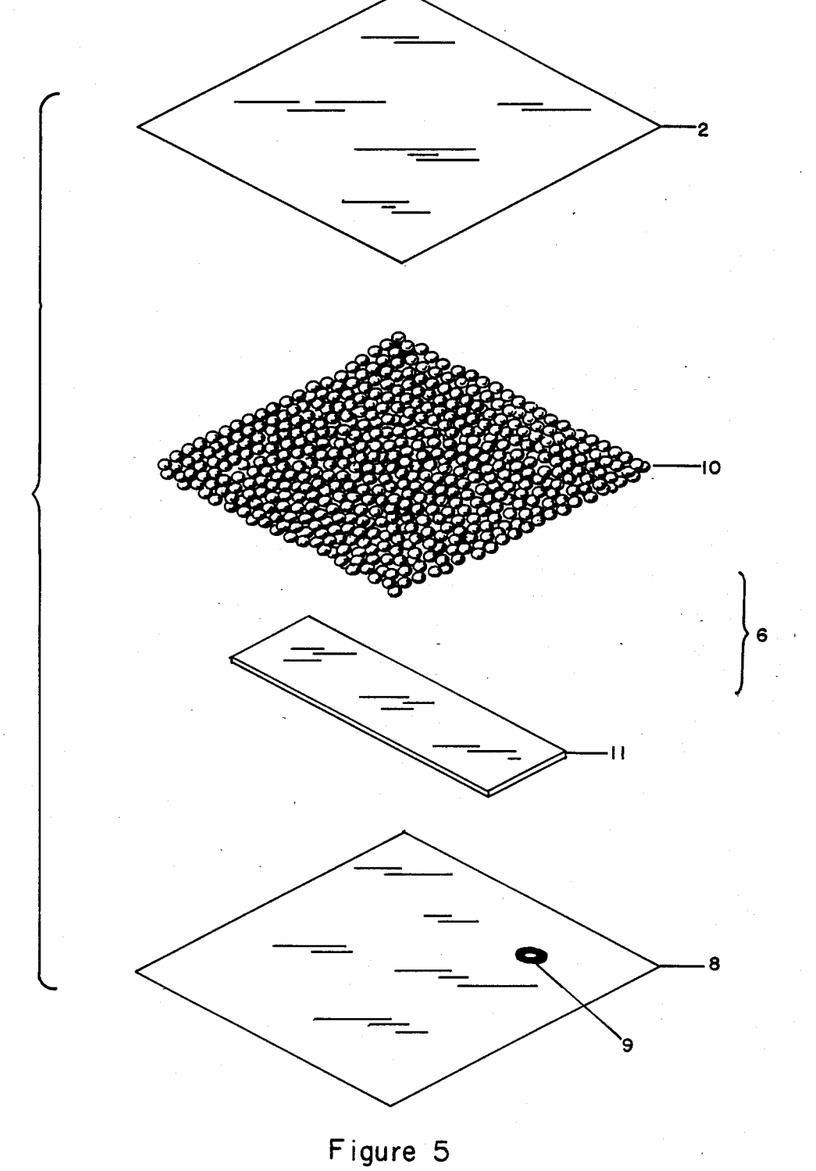
FIG. 5 is an exploded view of a mattress showing the location of an optional headboard.
Figure 6:
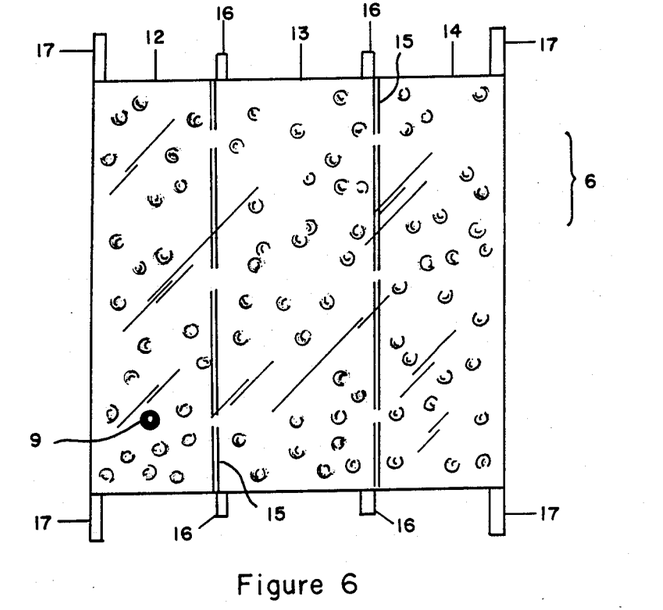
FIG. 6 is a top view of a basic infant restraint.
Figure 7:
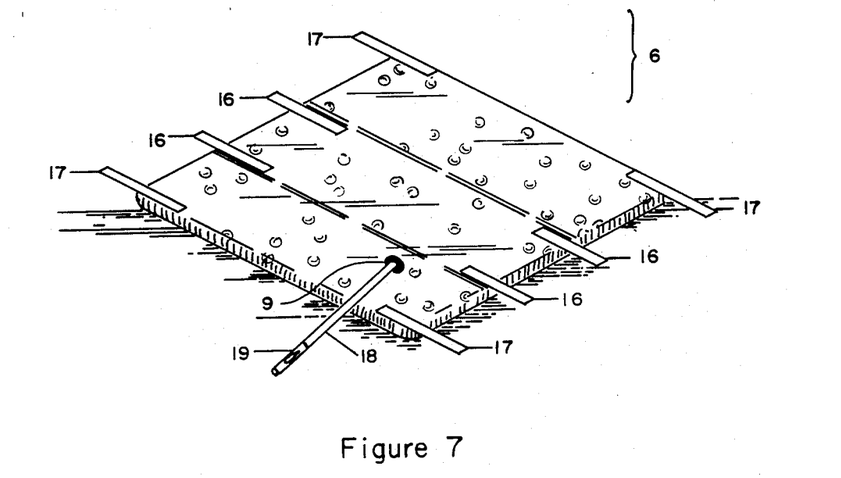
FIG. 7 is a bottom perspective view of the basic infant restraint of FIG. 6.

FIG. 5 is an exploded view of a mattress 6 including an upper sheet 7, a lower sheet 8 having a stoma 9 therein, a multiplicity of the cells 10 and a more-or-less rigid backboard 11. As shown in FIGS. 6 and 7, the mattress 6 includes several side-by-side sections 12, 13, 14 separated from each other by a series of longitudinal seals 15. The seals 15 allow passage of air therethrough but prevent the transfer of cells therethrough. The backboard 11 is positioned inside the central section 13 and is about the same length and width as the section 13. The backboard 11 comprises a support for an object or body in the mattress 6 and also affects the shape of the mattress after air is withdrawn from the envelope provided by the sheets 7, 8.

Means are provided for securing the mattress 6 about an object or body. To this end, a plurality of looped Velcro straps 16 are provided intermediate the sides of the mattress 6 and a knitted Velcro brand fastener strap 17 is placed on each corner thereof. As in the embodiment of FIGS. 1-4, the stoma 9 is secured to a tube 18 having a valve 19 or other closure therein.

To use the mattress 6 as a neonate carrier, the side sections 12, 14 are folded toward the center over the limbs and around the side of the head and body of the infant and the looped material of straps 16 are pressed onto the knitted strap 17 to close the mattress 6. Adhesive tape or Velcro brand fastener type closures 35, are applied to adjust the center opening to fit the individual infant. Then, air is withdrawn through the tube 18.

Figure 8:
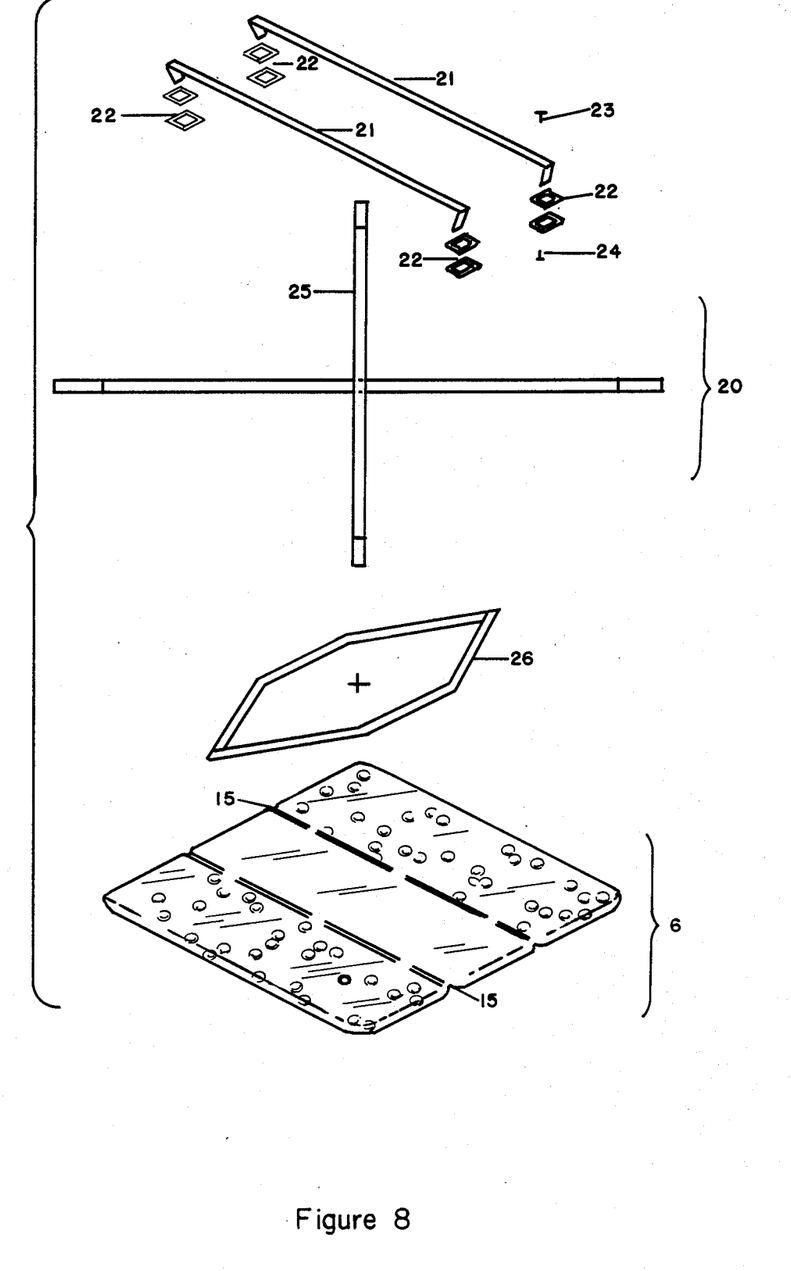
FIG. 8 is an exploded view of another embodiment of an infant restraint.

Referring to FIG. 8, the infant restraint mattress 6 is illustrated as including an alternate harness arrangement 20.

The parallel straps 21 are attached to the center section on the reverse side of the restraint along the edges of the backboard 11. Optional D-rings 22 are attached to the ends of each parallel strap 21. Optional rivets 23 and 24 reinforce this connection. The parallel straps 21 are attached to the lower sheet to leave spaces therebetween for the oblique straps 25 to move independently of the parallel straps 21. The handle straps 26 are secured to the reverse side of the mattress but are not attached to the parallel straps 21.

Figure 9:
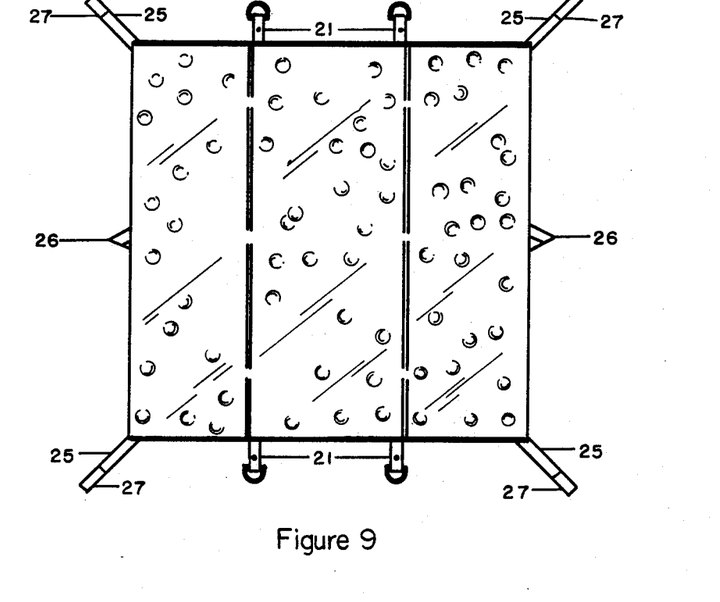
FIG. 9 is a top view of another embodiment of an infant restraint system.

Referring to FIG. 9, the top side of the infant restraint system of FIG. 8 is illustrated. The oblique straps 25 contain optional Velcro brand fastener 27 or a comparable knitted looped closure.

Figure 10:
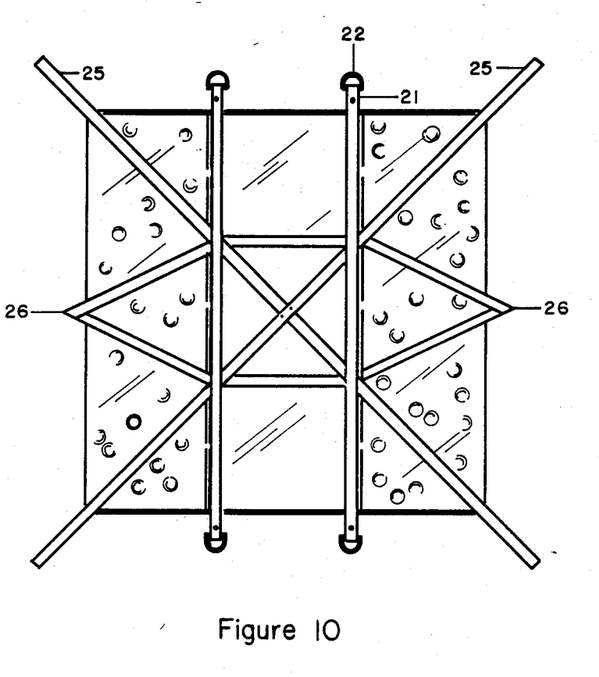
FIG. 10 is a bottom view of the infant restraint system of FIG. 9.
Figure 11:
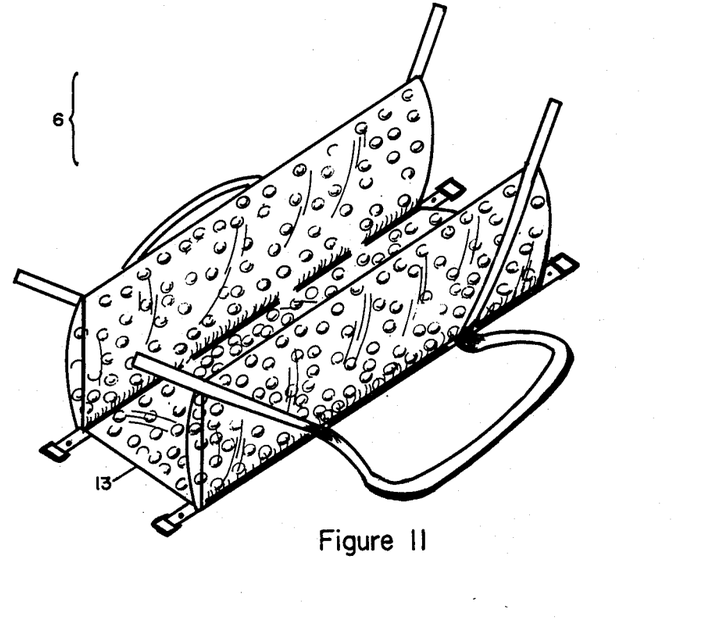
FIG. 11 is a perspective view of the infant restraint system of FIGS. 9 and 10.
Figure 12:
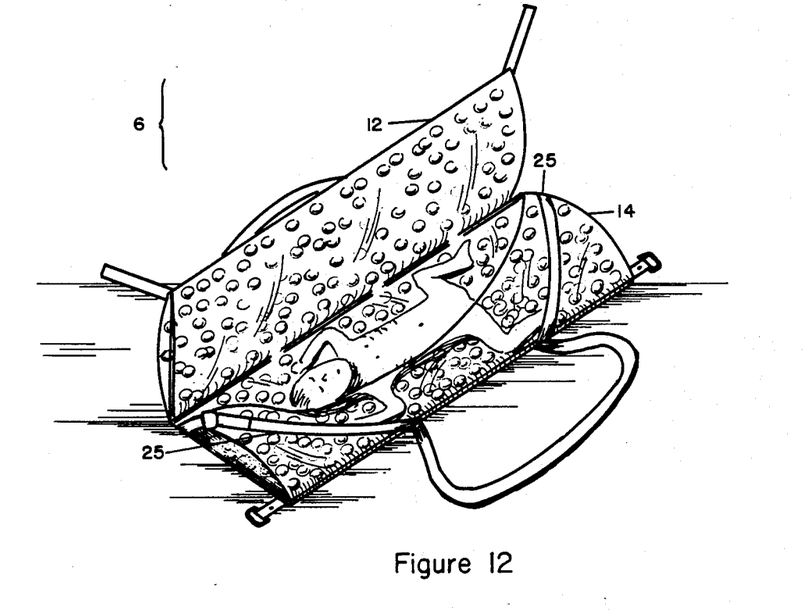
FIG. 12 is another perspective view of the infant restraint system of FIGS. 9-11 showing the device partially enclosing a neonate.

FIG. 10 shows the reverse side of the infant restraint system of FIG. 9. The parallel straps 21 with optional D-rings 22 are attached to the base leaving spaces for the oblique straps 25 to slide through between the back of the restraint and the parallel strap 21.

An alternate way to construct the harness 20 is to use the harness in the same configuration as described above, attaching it to the mattress with heat seal, ultrasound, or adhesive, or in any manner of satisfactory permanence.

The film material of the sheets 2, 8 as well as the material of the cells 10 are preferably transparent so the infant, neonate, or other protected article may be viewed through the mattress 6.

Referring to FIGS. 11-15, the mattress or restraint 6 is illustrated in use. An infant or neonate is placed on the central section 13 and the side section 14 is folded over the infant with the right oblique straps 25 secured to the left parallel straps 21 by means of the optional D-rings 22 and Velcro brand fastener type closures 27. The other side section 12 of the restraint 6 is placed to the side of the infant's body and to the side of the infant's head. The bubbles 3 are moved manually inside the envelope to leave a cleared pocket which provides access to the infant's limbs after the section 12 is securely fastened to the opposite parallel straps 21. Any excess bubbles or cells 3 are burst by manually squeezing on them through the transparent film material.

Free air inside the restraint 6 is evacuated through the tube 18 secured to or extending into the stoma 9. The valve 19 connects to a pump 28 and compresses the bubbles 3 into a desired shape thus creating a comfortable custom mold that fits the patient's body without constricting the patient.

Figure 14:
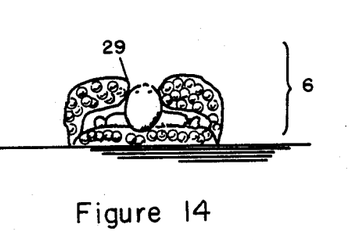
FIG. 14 is a cross-sectional view of the device of FIG. 13, taken substantially along line 14—14 of FIG. 13.

One of the peculiarities of the restraint 6 is that the pocket 29 around the infant, best seen in FIG. 14, is slightly larger than the infant. Accordingly, the restraint 6 of this invention does not squeeze the infant as one might expect. Before the air is evacuated from the restraint 6, the sections 12 and 14 rest lightly against the infant. It is thus apparent that evacuating air from the envelope of the restraint 6 causes the film of the sections 12, 14 adjacent to the infant to move upward away from the infant. This phenomenon occurs because the backboard 11 is in the section 13 and cannot deform the section 13 against the infant.

Figure 13:
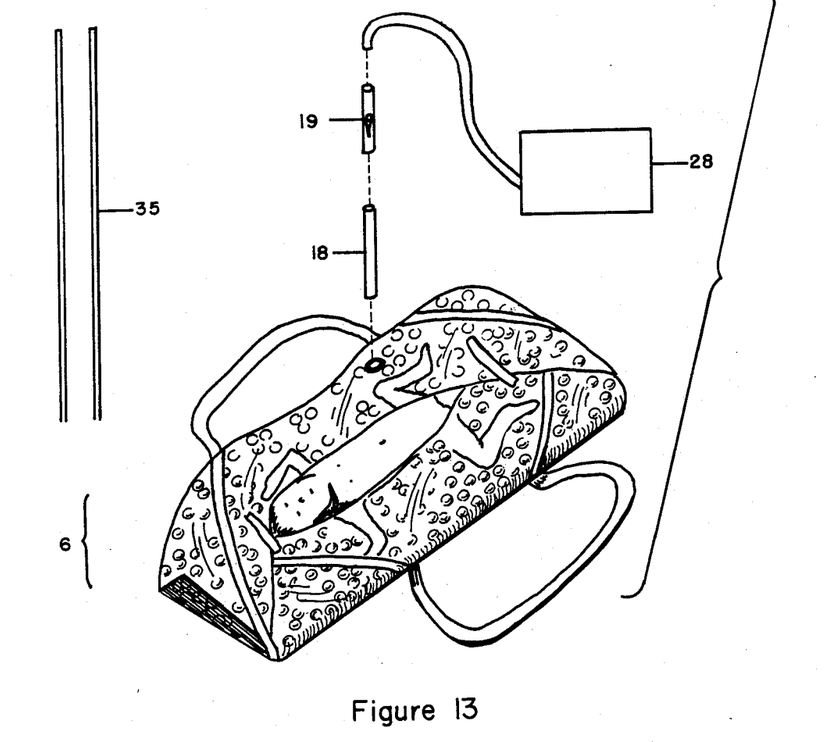
FIG. 13 is another perspective view of the device of FIGS. 9-12 showing the device enclosing a neonate.

As shown in FIG. 14, the infant is free to move slightly inside the pocket 29 and is accessible to a nurse or doctor through the gap between the free ends of the lateral sections 12, 14 as shown best in FIG. 13.

Figure 15:
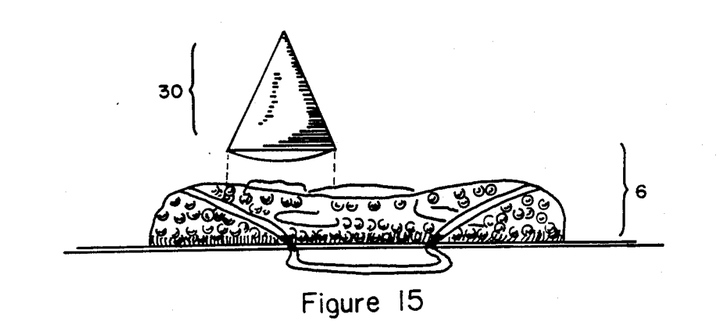
FIG. 15 is a side elevational view of the device of FIGS. 9-14.
Figure 16:
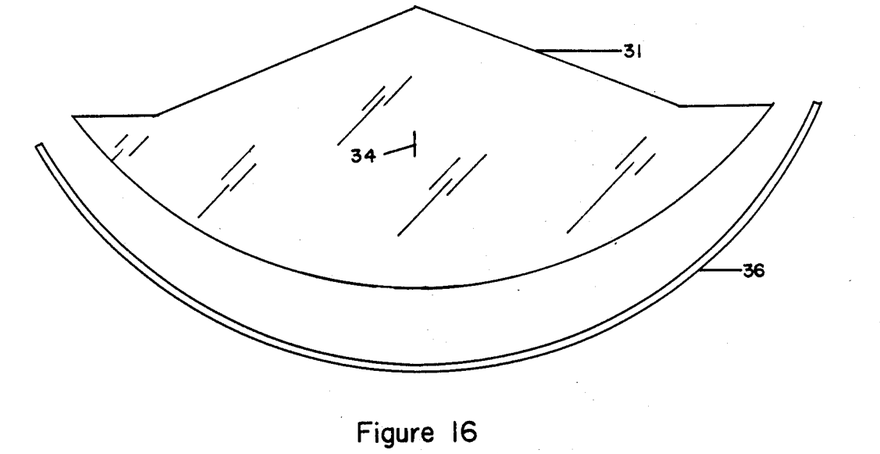
FIG. 16 is an exploded view of a disassembled flexible oxygen hood.
Figure 17:
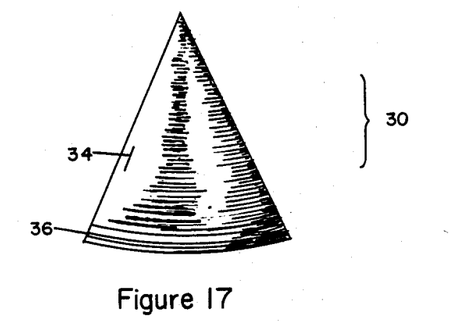
FIG. 17 is a side view of an assembled flexible oxygen hood.
Figure 18:
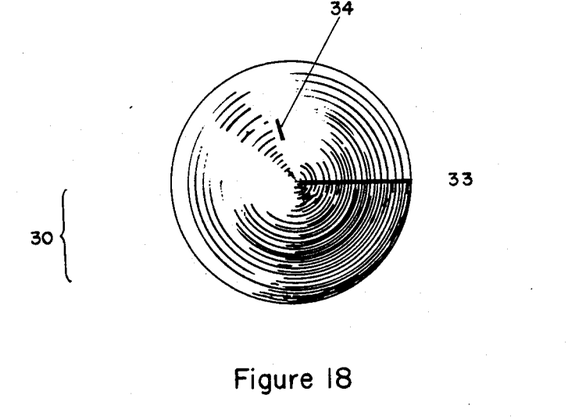
FIG. 18 is a top view of the assembled flexible oxygen hood of FIG. 17.

Referring to FIG. 15, an oxygen hood 30 is located directly above the infant's face. The hood 30 is conveniently cone-shaped and made from a flat piece of material 31 shown in FIG. 16. The material 31 is folded about a central axis 32 and held together by a seal 33 which may be achieved by heat, ultrasound, adhesive or any manner of satisfactory permanence. A flexible reinforcement 36 may be formed into a hoop and attached to the base of the hood. In use, the conical hood 30 is held in place over the patient's face by taping it to the mattress 6. A slit 34 receives a piece of tubing (not shown) connected to a source of oxygen (not shown). Because the infant is restrained by the device of this invention to relatively minor, short range movement inside the pocket 29, oxygen can confidently be delivered to the infant.

The above description shall not be construed as limiting the ways in which this invention may be practiced but shall be inclusive of many other variations that do not depart from the broad interest and intent of the invention.

I invention:

1. A lightweight apparatus evacuable into a shapable soft cushiony support for protecting a body during transport, comprising
    a flexible envelope having therein a fluid and a multiplicity of independently movable resilient fluid filled cells having a Shore A Durometer rating not greater than about 10; and
    means for evacuating the fluid from the envelope.

2. The apparatus of claim 1 wherein the envelope is 50-80% filled with the cells prior to energizing the evacuating means.

3. The apparatus of claim 1 wherein the cells are generally spherical in shape having an outer diameter greater than ¼".

4. The apparatus of claim 3 wherein the cells are generally spherical in shape having an outer diameter on the order of about 1".

5. The apparatus of claim 1 wherein the envelope comprises a plurality of separate sections, the sections being in fluid communication but not in cell exchanging relation.

6. The apparatus of claim 5 further comprising a rigid member received in a first of the sections, the rigid member being substantially the same size as the first section.

7. The apparatus of claim 6 wherein a second and a third of the sections lie on opposite sides of the first section, the second and third sections being manipulable to a position substantially overlying the first section.

8. The apparatus of claim 7 further comprising means for securing the second and third sections in the position overlying the first section.

9. The apparatus of claim 8 wherein the rigid member is of sufficient size to receive a baby and further comprising handles on the apparatus.

10. The apparatus of claim 1 wherein the cells are burstable by the application of manual pressure through the envelope.

11. The apparatus of claim 1 further means carried by the envelope for controlling the shape of the apparatus about the body after energizing the evacuating means, the controlling means comprising means for spacing the envelope from the body at least through a substantial portion of the periphery of the body.

12. The apparatus of claim 11 wherein the controlling means comprises a support in the envelope.

13. The apparatus of claim 12 wherein the envelope comprises a plurality of separate sections, the sections being in fluid communication but not in cell exchanging relation, the support being in a first of the sections, a second of the sections being foldable in juxtaposition to the first section.

14. The apparatus of claim 1 wherein the cells are unconnected.

15. The apparatus of claim 1 wherein the envelope comprises a plurality of separate interconnected sections out of cell exchanging relation and the evacuating means comprises means for evacuating each of the sections.

* * * * *